United States Patent [19]

Erickson

[11] Patent Number: 4,897,195
[45] Date of Patent: Jan. 30, 1990

[54] SYSTEM AND PROCESS FOR ANAEROBIC DIGESTION OF WASTE MATERIALS

[76] Inventor: Stewart E. Erickson, P.O. Box 4511, Ketchum, Id. 83340

[21] Appl. No.: 336,250
[22] Filed: Apr. 11, 1989
[51] Int. Cl.4 .............................................. C02F 3/28
[52] U.S. Cl. .................................. 210/603; 210/170; 210/179; 210/180; 210/241; 210/242.1
[58] Field of Search .............. 210/603, 619, 179, 180, 210/170, 747, 241, 242.1, 255, 96.1

[56] References Cited

U.S. PATENT DOCUMENTS

| | | | |
|---|---|---|---|
| 3,442,495 | 5/1969 | Schreiber | 210/619 X |
| 4,057,401 | 11/1977 | Boblitz | 210/180 X |
| 4,252,901 | 2/1981 | Fischer et al. | 210/603 X |
| 4,597,865 | 7/1986 | Hunt et al. | 210/179 X |
| 4,692,249 | 4/1987 | Hammel | 210/242.1 X |
| 4,789,469 | 12/1988 | Cvitas et al. | 210/179 X |

*Primary Examiner*—Tom Wyse
*Attorney, Agent, or Firm*—Gregory P. Kaihoi; James R. Haller; Mary P. Bauman

[57] ABSTRACT

The invention relates to a system and process for production of carbon dioxide, methane, and nitrogen rich fertilizers by anaerobic digestion of waste materials. The waste materials are digested in rotary digestion modules, and the chemical composition of the organic materials in the modules is monitored to determine the progress of the decomposition.

10 Claims, 3 Drawing Sheets

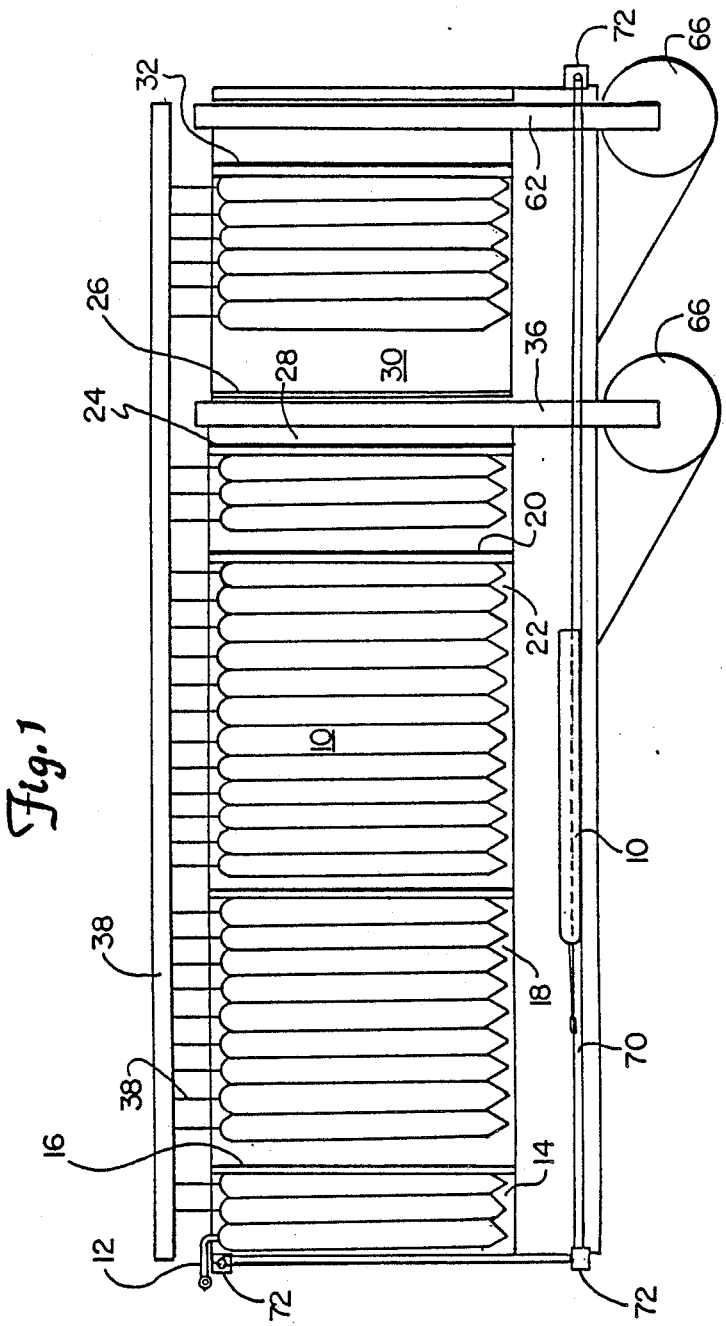

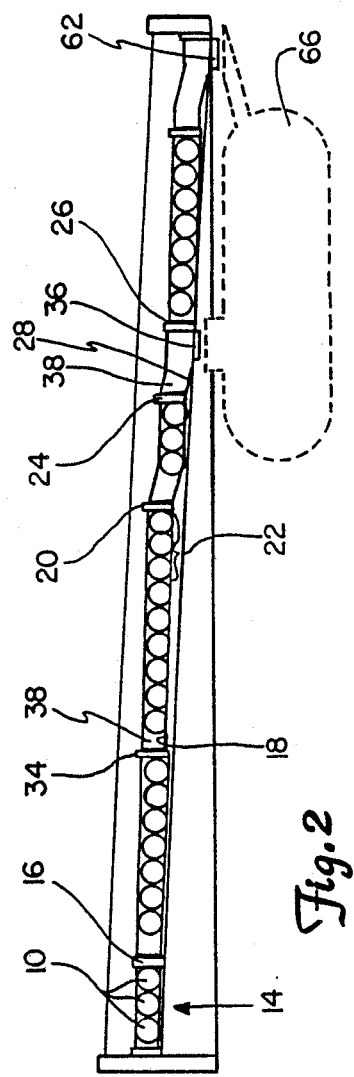
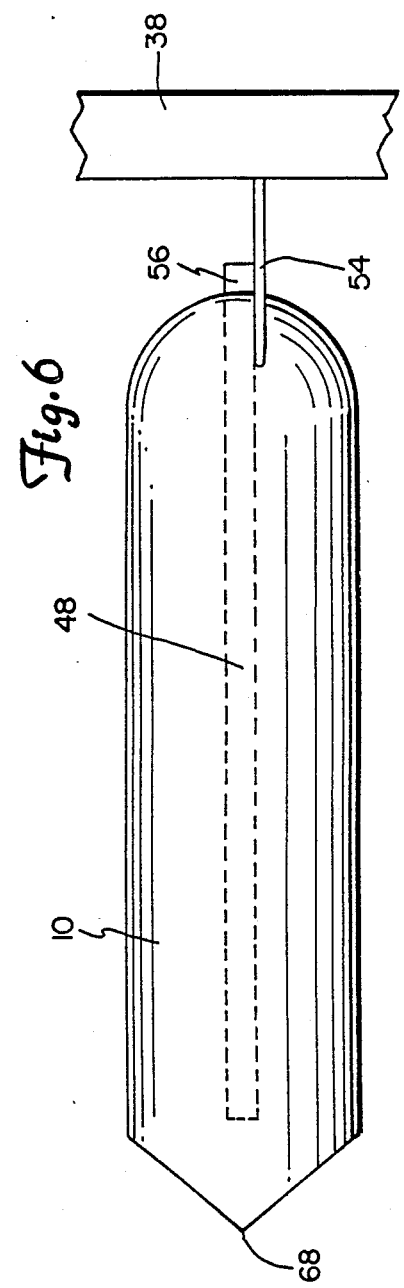

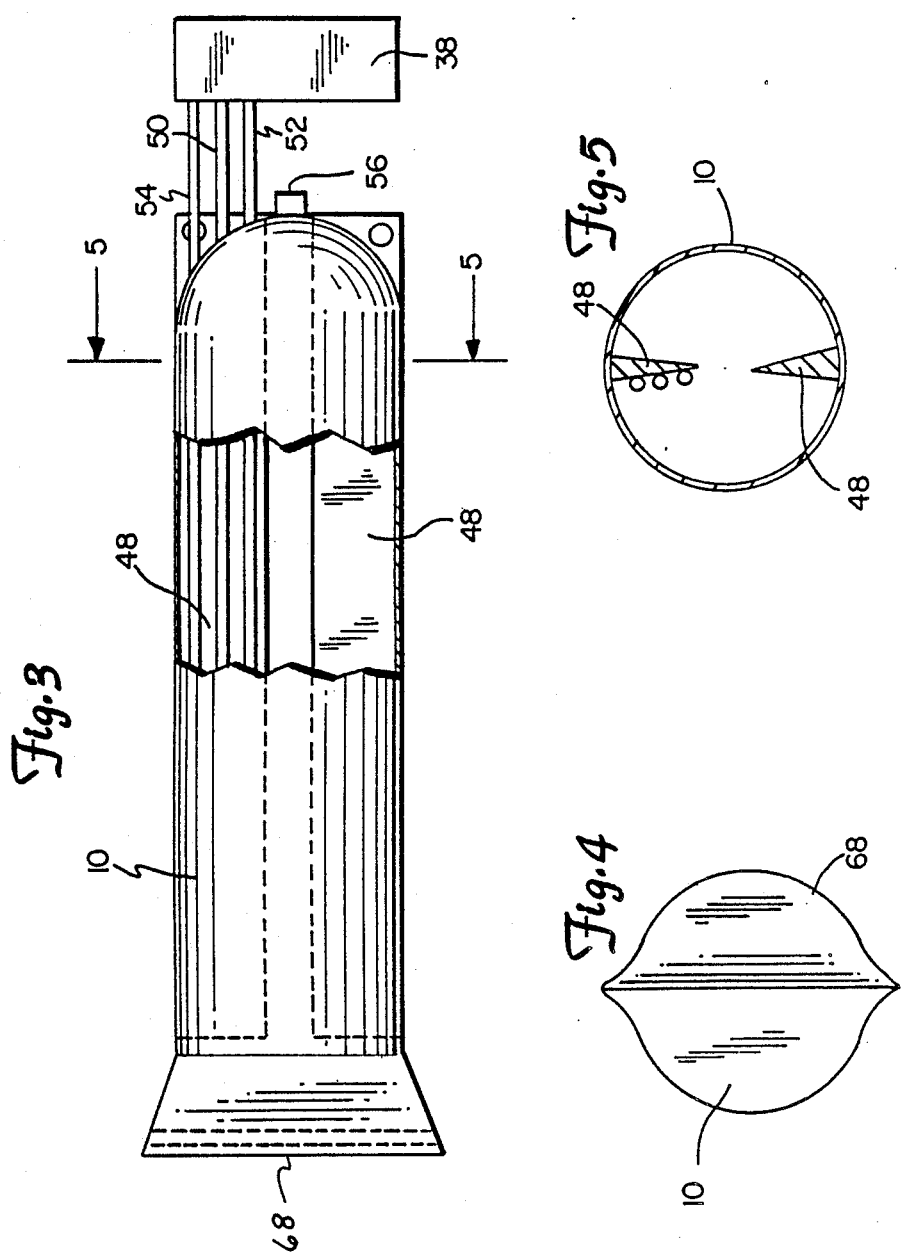

SYSTEM AND PROCESS FOR ANAEROBIC DIGESTION OF WASTE MATERIALS

FIELD OF THE INVENTION

The invention relates to a system and process for production of carbon dioxide, methane and nitrogen rich fertilizers by anaerobic digestion of waste materials.

BACKGROUND OF THE INVENTION

It has been known for many years that many organic materials will decay or decompose in time by either an aerobic process in the presence of oxygen or by an anaerobic process in the absence of oxygen. Aerobic and anaerobic decomposition processes are both naturally occurring biochemical processes that have been utilized for many decades.

The products of anaerobic decomposition include carbon dioxide ($CO_2$), methane ($CH_4$), and nitrogen rich solids, usually dispersed or dispersable in water, usuable as a fertilizer or soil conditioner. Methane has is an odorless, colorless, lighter-than-air gas that is commonly contained in natural gas. (Odor typically is added to natural gas to facilitate its detection.)

Anaerobic decomposition processes require an oxygen-free environment maintained at an elevated temperature. Insulated containers therefore may be used to accommodate and even hasten the naturally occurring decomposition process.

Generally in the United States and other highly industrialized countries, the prospect of processing waste materials to produce usable fuel alternatives have not been fully exploited. Research and development activities relating to waste materials typically have been concentrated on alternatives for safely disposing of such waste materials. Many of the projects undertaken for producing anaerobic digestion systems have concentrated on small scale digesters for the production of small amounts of methane gas by digestion of waste materials.

With our continuing dependence on fossil fuels and the most recent concern for the environment and the "greenhouse effect" that may be occurring due to the excess carbon dioxide emissions from the burning of these fossil fuels, it would be desirable to have a system and process for the efficient production of methane gas by anaerobic decomposition of suitable organic materials for use as an energy source for the future.

SUMMARY OF THE INVENTION

The present invention relates to a system and process for anaerobic decomposition of suitable organic materials for producing methane gas and soil conditioners. An objective of the present invention is to provide a system and process for anaerobic digestion which is economically feasible, efficient and environmentally compatible. The physical anaerobic digestion system of the invention includes a plurality of large, cigar-shaped, digester bags carried by an inclined floor, the digester bags being connected to a fluid exchange system which can add or take away fluids from the bags as desired. Each of the digester bags contains a digesting mixture of bacteria and waste materials which roll down the inclined floor helping to agitate the contents and to hasten the production of methane gas. In an alternative embodiment the bags may be maintained in a pond or pool, and therein mechanically rotated, either by rolling down an inclined floor or by other suitable means

BRIEF DESCRIPTION OF THE DRAWINGS

FIG. 1 is a top, somewhat schematic view of the anaerobic digestion system and process of the invention;

FIG. 2 is a side, elevational view of the anaerobic digestion system depicted in FIG. 1;

FIG. 3 is a side, partially broken away view of a digester bag of the invention;

FIG. 4 is a view of the left end of the bag of FIG. 3;

FIG. 5 is a cross-sectional view of the bag of FIG. 3 taken along the line 5—5 thereof; and FIG. 6 is a top view of the bag of FIG. 3.

DETAILED DESCRIPTION OF THE PREFERRED EMBODIMENT

The anaerobic digester of the invention comprises an efficient industrial method of converting a wide range of wastes including manures, refuse, human effluent, distillery by-products, vegetable by-products, and other materials into methane, carbon dioxide and a usable fertilizer. The process employs anaerobic digestion (i.e., digestion in the absence of oxygen) and produces carbon dioxide gas ($CO_2$), methane gas ($CH_4$), and nitrogen rich fertilizer material. The methane gas produced can be sold or burned and the fertilizer produced can be used to improve or reclaim land such as that land which has been strip mined.

A preferred anaerobic digestion system and process according to the invention is illustrated schematically in FIGS. 1 and 2. The system comprises a plurality of digester modules 10 which generally take the form of a somewhat flexible bag, the digester modules 10 lying on an inclined surface 18 enabling the modules to be rolled slowly, thus agitating the contents of the modules and facilitating the anaerobic digestion process. The digester modules 10 are filled with a suitable organic waste slurry generally at the uppermost end of the inclined surface 18 and allowed to slowly roll down the inclined surface 18 adjacent other digester modules 10 over a period of time sufficient to complete the anaerobic decomposition process, known as the digestor life cycle. The anaerobic digestion process takes place within the digester modules 10 and gases such as carbon dioxide and methane may be removed from the digester modules 10 while the digestion process is taking place as desired. Materials may also be added to the digester modules 10 to promote the digestion process or to change such factors as the pH level of the contents of the digestion modules 10 as desired without interrupting the digestion process.

As shown in FIGS. 1 and 2, the digester modules 10 preferably are aligned adjacent one another on an inclined plane surface 18 and are allowed to roll down the inclined surface 18 over a period of time to agitate the contents of the digester modules 10. The anaerobic digestion system may include a heating unit (not shown) for heating the contents of the digestion modules 10 to a temperature preferably between 100° and 140° F. to hasten the anaerobic decomposition process. The heating means may be contained within the digestion modules or externally of the digestion modules. The heating system preferably burns the methane gas produced by the digestion process, making the system economical to operate. Alternatively, resistance heating elements may be used to heat the organic material or any other suitable heating means. In one preferred embodiment, the modules 10 are housed in a solarium-type structure, taking advantage of passive solar energy. Alternately, the heating system could utilize waste heat, e.g., from coal-fired power plants. Such heat sources for a particular installation will ultimately be dependent on the relative costs of energy sources and availability of waste heat, solar heat, etc.

The environment in which the anaerobic digestion process is taking place should include an adequate gas relief system, as described in greater detail below, for removing the gases produced, in the process including methane and carbon dioxide. The anaerobic digestion system of the invention may also include testing means comprising a master gas control unit 38 for sampling the contents of the digestion modules to determine the extent of completion of the anaerobic digestion process taking place within the digestion modules and for determining what materials, if any, to add to promote the decomposition process.

In a preferred embodiment the digestion modules 10 themselves comprise generally cigar-shaped synthetic bags which are liquid-tight and provide an anaerobic environment in which materials can be digested. The materials from which the bags are constructed must be generally non-reactive so as not to interact with the digestion slurry. As shown in FIG. 3, the bags preferably include a plurality of fluid transfer ports allowing entry and exit of materials, including the organic material port 56, carbon dioxide and methane gas port/line 54, sampling line 50, and doping line 52 for various other substances that might be added to the digestion modules to facilitate the process.

The digestion bags are preferably generally circular in transverse cross section, enabling them to easily roll down an inclined surface. The external wall of the bags preferably has a smooth surface which will slip easily when placed adjacent an identical digester bag, the surface preferably having a very low static and kinetic coefficient of friction. The bags preferably also include hardware on their external side for lifting and moving them. They may also include internal agitation means for stirring and agitating the contents of the bag to promote the decomposition process and to move substances contained within the bag to a favorable location to be easily removed from the bag. The agitation means may comprise a plurality of agitator paddles 48, shown in FIGS. 3 and 5, contained within the digester bag 10 for agitating the contents of the bag as they roll down the incline 18. The agitator paddles 48 or another portion of the interior of the digester bag 10 may contain sampling locations from which specific materials contained within the digesting bags can be sampled and removed. In a preferred embodiment, the sampling, doping and gas lines 50, 52 and 54, respectively, may be suitably attached to an agitator paddle to facilitate in adding and extracting materials to and from selected portions of the module.

The emptying means on the digester modules 10 may comprise a closable opening for draining the contents as by pumping or alternatively may include a generally larger opening, such as that shown as 68 in FIGS. 3 and 4, enabling the contents to be dumped and may be of any suitable closable type.

In a preferred embodiment, the anaerobic digestion system of the invention operates as follows. The process is begun by placing the digester modules 10 in an area at the highest point of the inclined planar floor. The uppermost portion of the inclined planar floor is referred to as the digester head 14. The digestion modules 10 are arranged on the digester head 14 as shown in FIGS. 1 and 2 where they are filled with the organic material to be processed. Sampling and material transfer lines 50, 52, 54 are connected to each digestion module 10 as shown in FIG. 3. Although the digesting modules 10 are nearly filled with organic material, some volume is left for expansion as gases are produced in the anaerobic decomposition process. Living anaerobic bacteria are added to the organic material within the digestion module along with carbon dioxide gas and lignite (See, e.g., U.S. Pat. No. 3,640,846). The contents of the digestion module are chemically balanced through doping for optimum bacterial growth. Preferably more than one digestor module 10 is prepared in this manner on the digester head 14 before being released by the head gate 16. The head gate 16 is a movable barrier between the digester head 14 and the inclined planar surface 18 for retaining the digester modules 10 on the digester head 14 until they are ready to be released onto the inclined surface 18. The head gate 16 may comprise a sturdy steel gate rising up out of the inclined floor to stop the forward roll of the bags 10 off of the digester head 14. When the gate is moved out of the way of the digesting bags 10, the bags are allowed to roll onto the inclined surface 18 enabling the digestion life cycle to commence.

The digester modules 10 are allowed to roll slowly in close contact with one another along the inclined surface 18 with their axes aligned generally parallel with one another. The material transfer lines and sampling lines 50, 52, 54 attached to the digestion modules for communication between the master gas control unit 38 and the digestor modules 10 are preferably in free rotating engagement with the master gas control unit and remain connected to the digestion modules throughout their entire journey down the inclined plane 18 of the digester. The master gas control unit 38 extends along the length of the inclined surface 18 to continuously monitor the progress of the anaerobic decomposition process taking place inside of the digester modules 10 as the modules move along the inclined plane 18. The digestion modules 10 are sampled by the computer controlled master gas control unit which monitors the contents of the digesting modules 10 and automatically dopes the contents of the digestion modules 10 as desired for the most efficient anaerobic decomposition.

The angle of the inclined plane 18 with respect to horizontal may vary from one system to the next depending on several variables, including the size of the digester modules 10, how full they are, how rigid they are, etc. In most systems the angle would be between about 0.1° and 5°, desirably between about 0.2° and 3°, and most preferably about 1°. The determinative factor is that the angle be steep enough to enable the digestion modules 10 to roll slowly down the inclined plane 18 while in close contact with other digestion modules but flat enough to prevent the digestion modules 10 from attaining excessive momentum.

Any number of positioning gates 34 may be included along the inclined plane 18 for retarding movement of the digestion modules 10 to space the modules or to otherwise adjust the positioning of the modules as desired. For example, a separate gate might be included for each module 10, but it is anticipated that most installations could accommodate at least several modules 10 per gate, depending on their size.

The lower end of the inclined plane comprises a digester tail 22 preferably sized to hold three digestion modules 10 carried by the inclined plane 18. A tailgate 20 is positioned at the end of the digester tail 22 for stopping the digester modules 10 from moving forward down the inclined plane 18. The tailgate 20 is movable to allow one or more digestion modules 10 at a time to roll off of the digester tail 22 down an accelerator ramp 28 and onto either a conveyor for removal or onto an extended cycle incline 30, depending on the extent of completion of the decomposition process. The majority of the digestion modules reaching the end of the inclined plane will have completed the anaerobic digestion process and will be ready to have their contents emptied.

In order to empty the digestion modules, a separating gate 24 is moved to allow the digestion modules that have passed by the tailgate 20 to roll down an acceleration ramp 28 and onto a conveyor belt 36 where they are restrained from moving any further by an extended cycle head gate 26. The conveyor belt 36 moves in a direction in alignment with the axes of the digester modules 10 to remove the digester modules 10 from the inclined plane 18 for emptying. The digester modules 10 may be emptied by pumping the contents out through an opening or by forcibly dumping them into a slurry receptacle such as the tank 66 shown in FIG. 2. When the emptying process is complete, the empty digestion modules are returned to the digester head 14 where they are refilled and reused.

The transporting means used to move the digester modules from the conveyor belts to the digester head may, in a preferred embodiment, comprise a motorized cable system 60, as shown in FIGS. 1 and 2, for dragging the digestion modules 10 along a smooth surface. The conveying system comprises a plurality of support towers 72 between which extends a continuous cable 70 to which the modules may be attached. Other transporting means may be employed as desired.

When a digester module 10 reaches the separating gate 24 adjacent the emptying conveyor belt 36 containing organic material that has not been fully digested the separating gate 24 is opened, allowing the digester module 10 to roll down an acceleration ramp 28, across the conveyor belt 36 and past a retracted extended cycle head gate 26 where it enters an extended cycle incline 30 similar to the incline previously described. On the extended cycle incline 30, the digester modules 10 are allowed to continue the anaerobic digestion process to completion while still being monitored by the master gas control unit 38. The extended cycle incline 30 allows the digester modules 10 to complete the anaerobic digestion process before they are emptied and returned to the digester head 14. A tailgate 32 is included with the extended cycle incline 30 at its lower end to retain the digester modules 10 on the extended cycle incline 30 while the contents are still being processed. When the anaerobic digestion process has been completed within the digester modules 10, the tailgate 32 is moved to a position to allow the digester modules 10 to pass by and proceed down an acceleration ramp 64 to a second conveyor belt 62 for removal. The digester modules 10 are removed in the same manner as previously described and returned to the digester head 14 for reuse.

In an alternative embodiment, rather than rolling on an inclined plane the modules 10 are floated in a pond or pool of controlled temperature water. Rotation of the modules 10 to agitate the contents may then be accomplished mechanically, either manually at desired intervals or automatically by suitable mechanical linkages to a drive motor. Alternately, an inclined floor may be utilized in conjunction with such a pool Filling and emptying of the modules can be carried out as with the inclined embodiment.

While a preferred embodiment of the present invention has been described, it should be understood that various changes, adaptations and modifications may be made therein without departing from the spirit of the invention and the scope of the appended claims.

What is claimed is:

1. A system for digestion of an organic waste slurry, comprising:
   a plurality of digestion modules, each having a waste inlet port, a gas discharge port, and means for agitating the waste contained within the digestion module in response to rotation of the module; means for filling the digestion modules with the organic waste slurry; rotation means for causing controlled rotation of the modules during the digestion process;
   means for maintaining the temperature of the digestion modules within a selected range;
   gas collection means operatively connected to each of the digestion modules for collecting gases produced in each of the digestion modules; and
   means for emptying the slurry from each module upon completion of digestion therein;

2. The system of claim 1 wherein the rotation means comprises:
   an inclined floor upon which the modules rest, the modules being urged to roll down the incline by gravitation; and
   means for selectively and controllably restraining the modules from rolling down the inclined floor, such restraining means being operative to permit controlled rotation of the modules as they roll down the inclined floor.

3. The system of claim 1 including a fluid pond in which the modules float.

4. The system of claim 3 in which the rotation means comprises mechanical means operatively connected to each module to rotate it as it floats in the pond.

5. The system of claim 1 further including a system enclosure for maintaining the ambient temperature around the modules within a predetermined range.

6. The system of claim 5 wherein the system enclosure is configured and arranged to receive and retain solar radiation to at least partially heat the interior of said enclosure.

7. The system of claim 1 wherein the agitating means within each module comprises a plurality of radially extending agitator paddles.

8. The system of claim 1 wherein each module is comprised of a flexible material.

9. A system for the production of methane gas, carbon dioxide gas and fertilizer material by the anaerobic digestion of suitable organic materials comprising:
   a plurality of digestion modules;
   a filling means for filling the digestion modules with organic materials;
   an inclined planar surface for supporting the digestion modules;
   monitoring means for monitoring the contents of the digestion modules, adding materials to the modules, and extracting gases from the modules, movement control means for controlling movement of the digestion modules upon the inclined planar surface, extraction means for removing the digestion modules from the planar surface, emptying means for emptying the contents of the digestion modules, transporting means for transporting the digestion modules, and agitation means for agitating the contents of the modules as they move down the planar surface to promote the digestion process.

10. A process for digestion of organic waste materials, comprising the steps of:

injecting the organic material into a tabular-shaped digestion module where the decomposition process occurs;

agitating the organic material contained within the module by rotating the module to promote the decomposition process;

monitoring the organic material contained in the module to determine chemical composition and progress of the decomposition process;

adding water, liquid effluent and other substances as necessary to the contents of the module to promote efficient decomposition;

extracting gases produced during decomposition from the module; and removing the remaining slurry when the decomposition process has reached a selected stage.

* * * * *